United States Patent
Shin

(10) Patent No.: US 11,584,924 B2
(45) Date of Patent: Feb. 21, 2023

(54) METHOD FOR CONCENTRATING MICROORGANISM OR EXTRACTING NUCLEIC ACID USING DTBP

(71) Applicant: INFUSION TECH, Anyang-si (KR)

(72) Inventor: Yong Shin, Seoul (KR)

(73) Assignee: INFUSION TECH, Anyang-si (KR)

( * ) Notice: Subject to any disclaimer, the term of this patent is extended or adjusted under 35 U.S.C. 154(b) by 932 days.

(21) Appl. No.: 16/326,376

(22) PCT Filed: Aug. 24, 2017

(86) PCT No.: PCT/KR2017/009254
§ 371 (c)(1),
(2) Date: Feb. 19, 2019

(87) PCT Pub. No.: WO2018/038549
PCT Pub. Date: Mar. 1, 2018

(65) Prior Publication Data
US 2021/0284990 A1    Sep. 16, 2021

(30) Foreign Application Priority Data

Aug. 24, 2016 (KR) .................. 10-2016-0107827
Aug. 24, 2017 (KR) .................. 10-2017-0107007

(51) Int. Cl.
| C12N 15/10 | (2006.01) |
| B01L 3/00 | (2006.01) |
| C12N 1/02 | (2006.01) |
| C12Q 1/24 | (2006.01) |

(52) U.S. Cl.
CPC .... *C12N 15/1006* (2013.01); *B01L 3/502753* (2013.01); *C12N 1/02* (2013.01); *C12N 15/1013* (2013.01); *C12Q 1/24* (2013.01)

(58) Field of Classification Search
CPC .......... C12N 15/1006; C12N 1/02; C12N 15/1013; B01L 3/502753; C12Q 1/24; C12Q 1/6806; C12Q 2527/125
See application file for complete search history.

(56) References Cited

U.S. PATENT DOCUMENTS

| 5,665,582 A * | 9/1997 | Kausch .............. C12N 15/1006 536/3 |
| 7,960,180 B2 * | 6/2011 | Chang .................... B01D 15/00 435/5 |
| 2003/0152932 A1 | 8/2003 | Kumar |
| 2011/0144190 A1* | 6/2011 | Davis .................. A61K 31/337 514/449 |
| 2012/0101230 A1 | 4/2012 | Wang et al. |
| 2012/0252702 A1* | 10/2012 | Muratani ............. C12Q 1/6846 435/6.12 |
| 2013/0137094 A1 | 5/2013 | Espina et al. |
| 2013/0149705 A1 | 6/2013 | Aurich-Costa |
| 2015/0030669 A1 | 1/2015 | Platscher et al. |
| 2015/0322486 A1 | 11/2015 | Shin et al. |
| 2016/0215325 A1 | 7/2016 | Kshirsagar et al. |

FOREIGN PATENT DOCUMENTS

| JP | 64-26520 A | 1/1989 |
| JP | 2016-501028 A | 1/2016 |
| JP | 2016-140289 A | 8/2016 |
| KR | 10-2013-0128348 A | 11/2013 |
| KR | 10-2014-0134710 A | 11/2014 |
| KR | 10-2015-0096444 A | 8/2015 |
| WO | 99/55825 A1 | 11/1999 |

OTHER PUBLICATIONS

International Search Report for PCT/KR2017/009254 dated Dec. 21, 2017 from Korean Intellectual Property Office.
Kajiura, Lauren N. et al., "Simultaneous Extraction of Viral and Bacterial Nucleic Acids for Molecular Diagnostic Applications", Journal of Biomolecular Techniques, 2015, vol. 26, pp. 118-124.
Yong Shin et al., "Dimethyl adipimidate/Thin film Sample processing (DTS); A simple, low-cost and versatile nucleic acid extraction assay for downstream analysis", Scientific Reports, vol. 5, Sep. 15, 2015, Article No. 14127.
Vladimir S. Trubetskoy et al., "Self-assembly of DNA-polymer complexes using template polymerization", Nucleic Acids Research, 1998, vol. 26, No. 18.
V. Charulatha, A. Rajaram, "Dimethyl 3,3'-dithiobispropionimidate: A novel crosslinking reagent for collagen", Journal of Biomedical Materials Research, 2001, vol. 54, pp. 122-128.
Thomas J. O et al., "Cross-linking of histone H1 in chromatin", Eur J Biochem. Dec. 1980, 112(3):501-511.
Qing Liu et al., "Two-stage sample-to-answer system based on nucleic acid amplification approach for detection of malaria parasites", Biosens Bioelectron. Aug. 15, 2016;82:1-8.
E Kotthaus et al., "Cross-linking of histones with dimethyl 3,3'-dithiobispropionimidate. Interference by a one-end reaction modifying histones at lysine amino groups", Biochem J. Dec. 15, 1984;224(3):1019-1022.
Naoyuki Fujita et al., "Use of bifunctional cross-linking reagents in mapping genomic distribution of chromatin remodeling complexes", Methods. May 2004;33(1):81-85.
Choong Eun Jin et al., "Use of Dimethyl Pimelimidate with Microfluidic System for Nucleic Acids Extraction without Electricity", Anal Chem. Jul. 18, 2017;89(14):7502-7510.
I Bakaltcheva et al., "Reversible cross-linking and CO treatment as an approach in red cell stabilization", Cryobiology. Jun. 2000;40(4):343-59.

* cited by examiner

*Primary Examiner* — Narayan K Bhat
(74) *Attorney, Agent, or Firm* — Revolution IP, PLLC

(57) ABSTRACT

A method for concentrating microorganisms, includes modifying an object by introducing an amine group into the object (step 1); and contacting a sample including a microorganism and dimethyl 3,3'-dithiobispropionimidate (DTBP) each other on the modified object (step 2), wherein the object is any one of a thin film device, a magnetic bead, a ring resonator, and a nanoparticle.

11 Claims, 8 Drawing Sheets

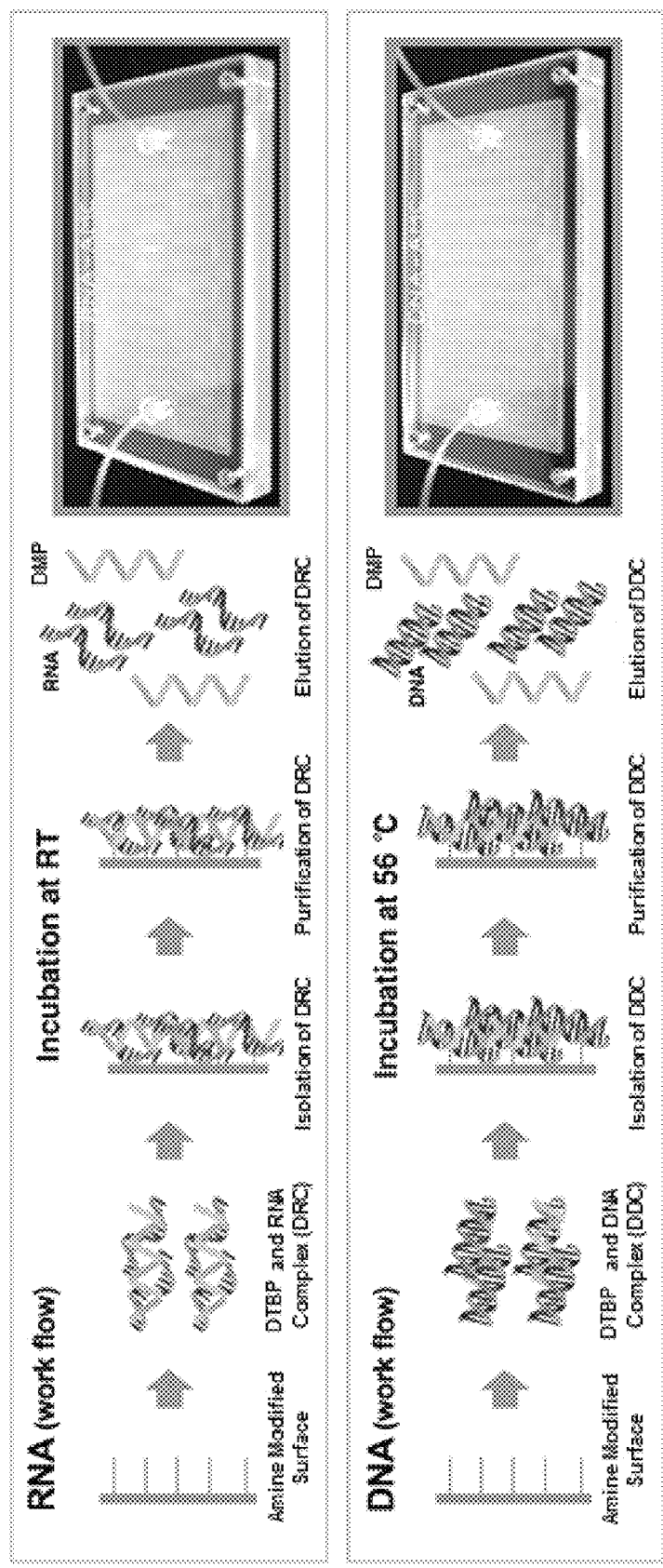
[FIG. 1]

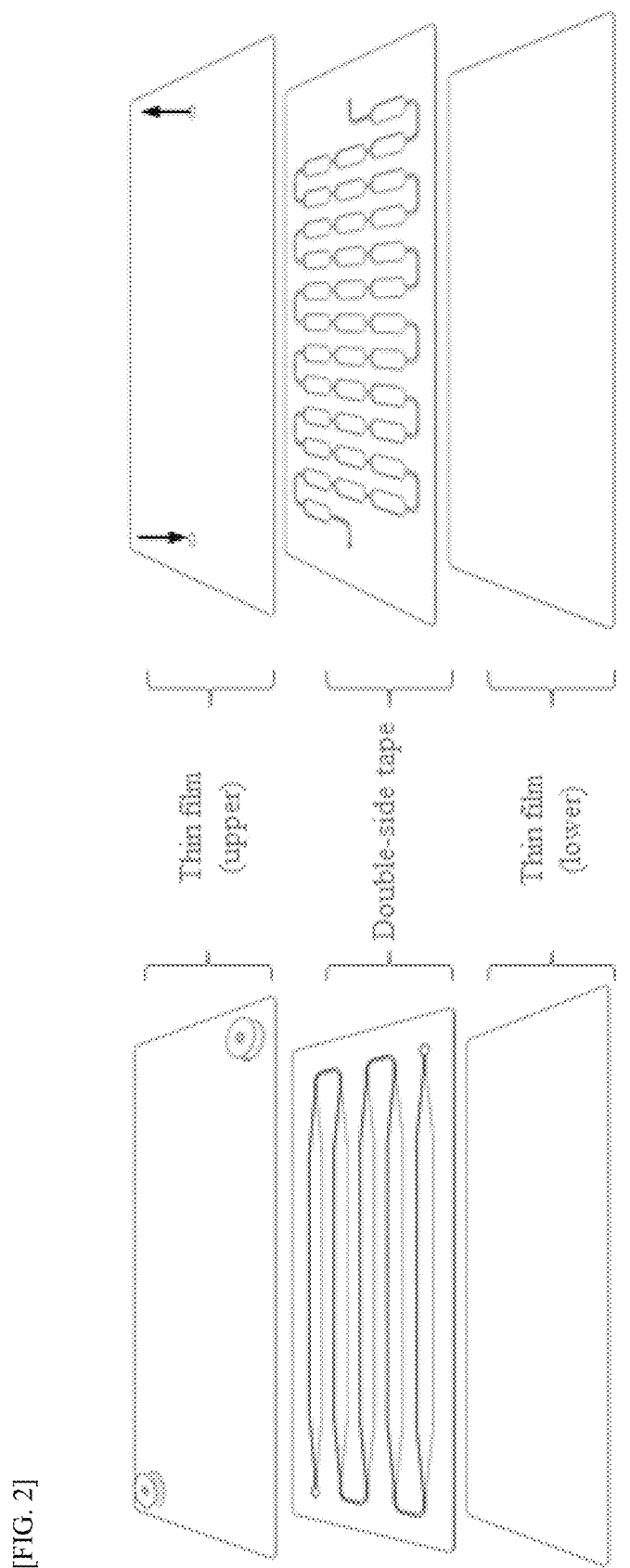
[FIG. 2]

[FIG. 3]
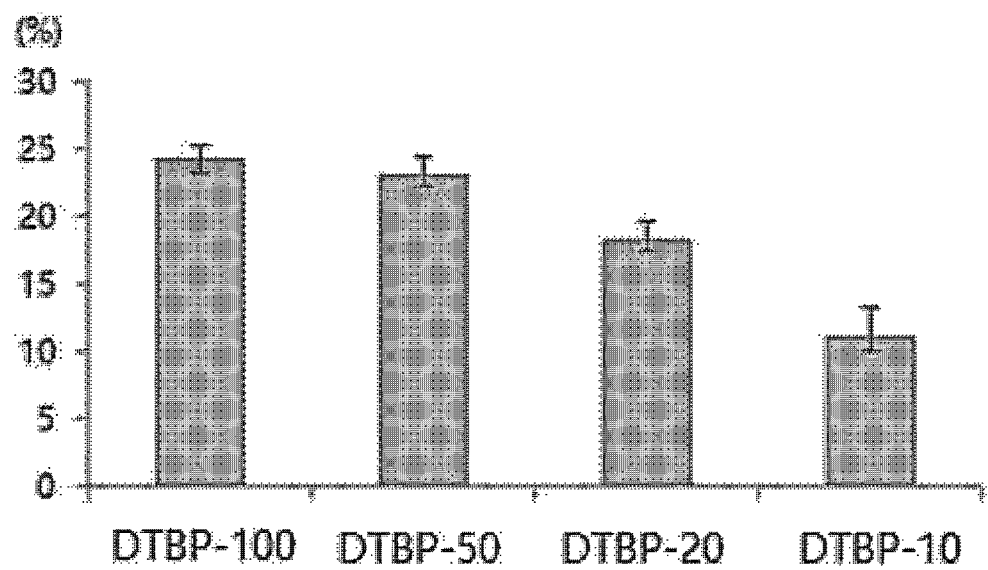

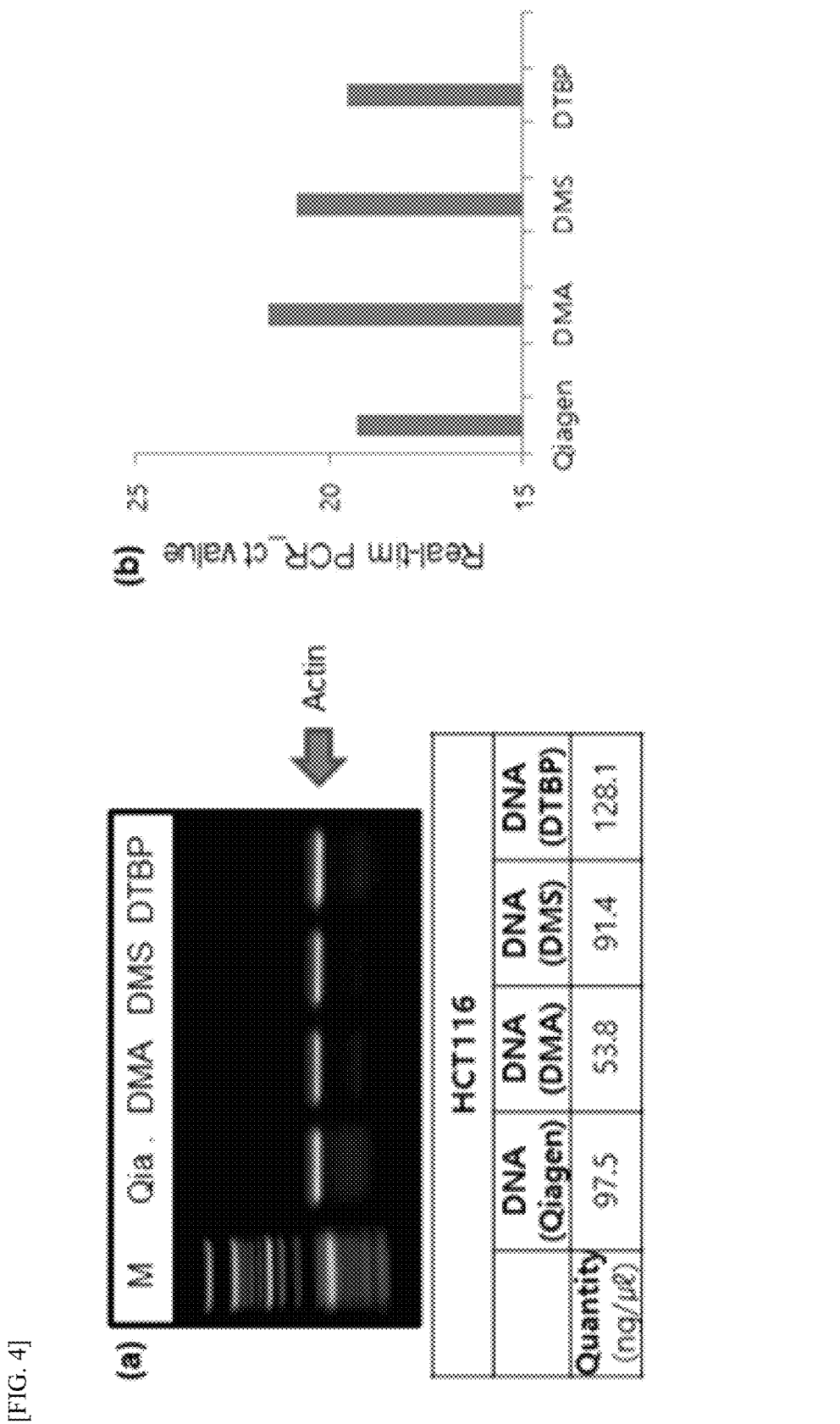
[FIG. 4]

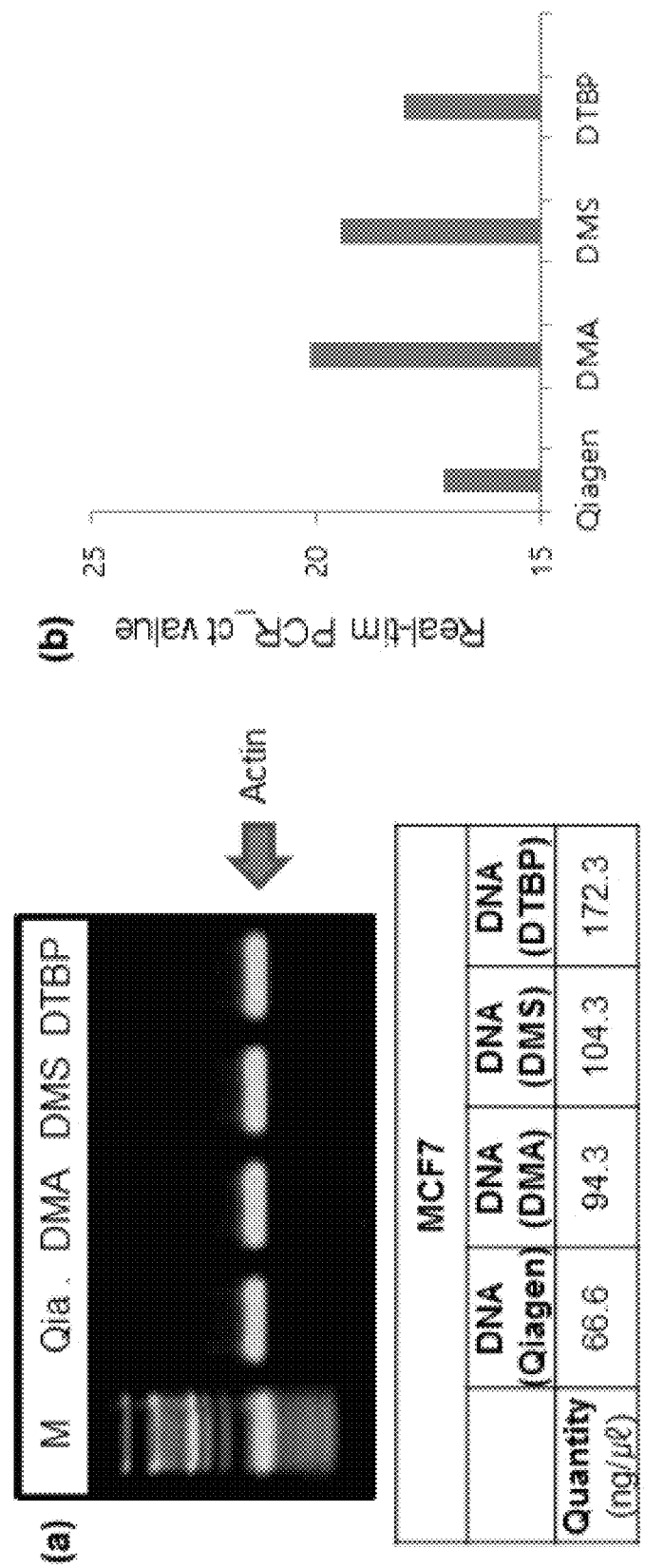
[FIG. 5]

[FIG. 6]
[FIG. 7]
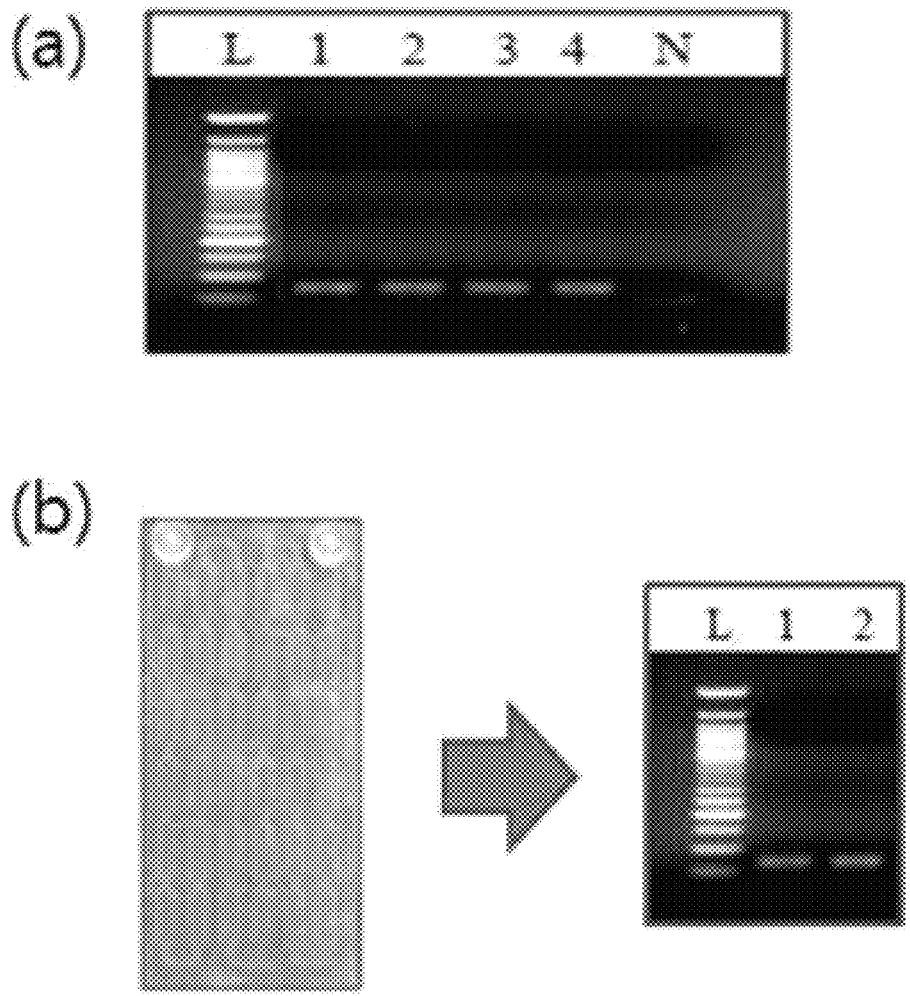

[FIG. 8]
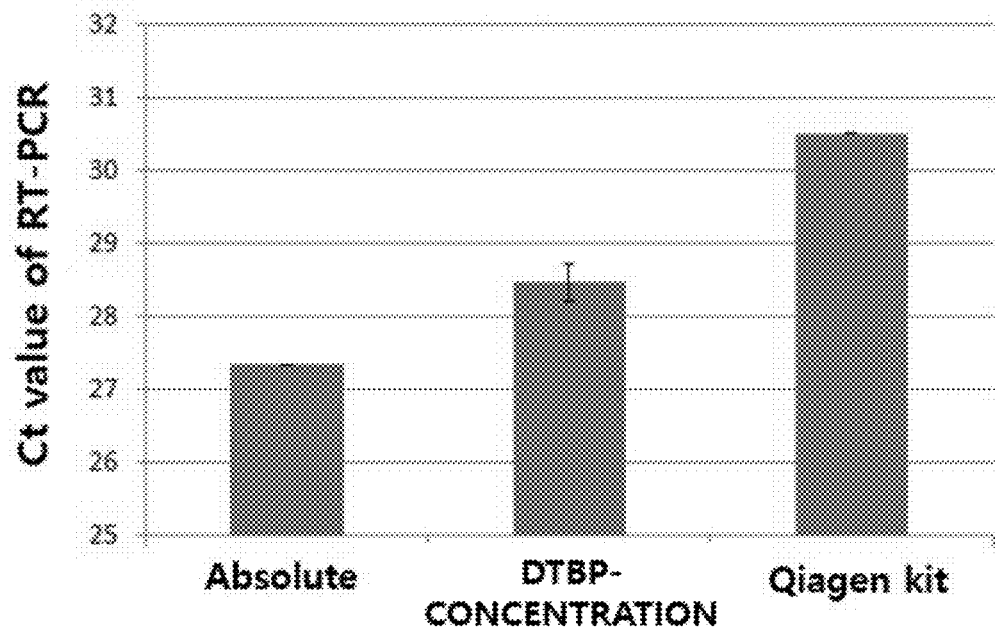
[FIG. 9]
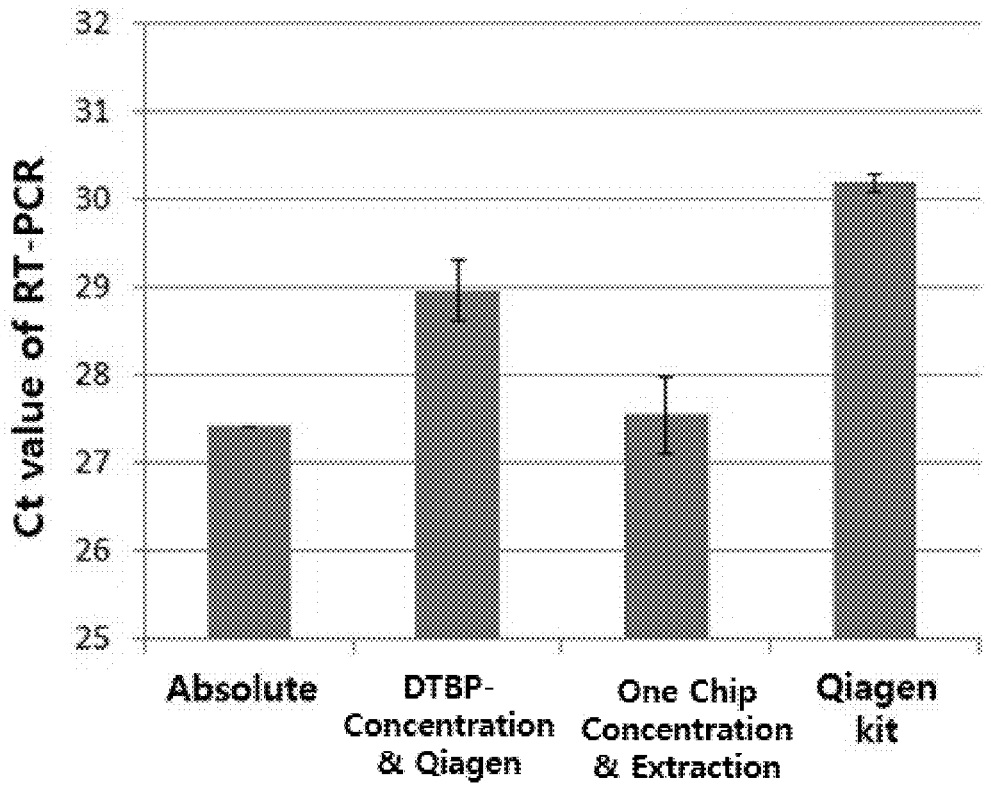

[FIG. 10]

METHOD FOR CONCENTRATING MICROORGANISM OR EXTRACTING NUCLEIC ACID USING DTBP

TECHNICAL FIELD

The present invention relates to a method of concentrating a microorganism or extracting a nucleic acid using dimethyl 3,3'-dithiobispropionimidate.

BACKGROUND ART

A nucleic acid is an important analytical tool for checking a disease state. A deoxyribonucleic acid (DNA) biomarker, such as single nucleotide polymorphism (SNP), a mutation, or DNA methylation, assists researchers to finds causes of cancer and provides important clues for providing great opportunities to diagnose and observe a disease state at an incipient stage of the disease and to prognose and monitor the disease state.

Since a nucleic acid such as DNA is present at a very low physiological concentration as compared with other components such as a protein (for example, tens of nanograms of the DNA are present with respect to tens of micrograms of the protein per microliter of whole blood), an effective extraction and preconcentration of DNA from a clinical sample is very important for subsequent processes such as amplification and detection processes.

In the existing methods for detecting a microorganism, a nucleic acid has been extracted using a portion but not all of 1-2 ml of a solution of a patient sample, and detection has been performed using the extracted nucleic acid. There is no major problem in the case of a large amount of a microorganism. However, in the case of a small amount of a microorganism, the microorganism may not be accurately detected, and thus, there may be a problem in adjusting additional infectious diseases. Therefore, there is a need to research a concentrating method, by which all microorganisms are used as much as possible from 1-2 ml of a sample.

In addition, recently, as the requirement for a highly purified nucleic acid has been increased in various fields including biotechnology, diagnostics, pharmacology, and metabolomics, attempts have been made to more rapidly isolate a nucleic acid with a higher purity from various biological samples.

However, the most advanced in a method of isolating a nucleic acid so far is technology for a carrier to specifically adsorb a nucleic acid among various materials, such as genomic DNA, plasmid DNA, messenger RNA, protein, and cell debris, which are included in a cell lysis solution. Almost all research to develop a method for isolating a nucleic acid has been focused on the research and development of materials to adsorb a nucleic acid.

Accordingly, in order to more rapidly isolate a nucleic acid with a higher purity, there is an urgent need to develop technology capable of isolating only a desired nucleic acid from cell debris, denatured protein aggregate, and other various materials in cell lysates.

DISCLOSURE

Technical Problem

The present invention is directed to provide a composition for concentrating a microorganism, including dimethyl 3,3'-dithiobispropionimidate (hereinafter, referred to as "DTBP") as an active ingredient and a method and a kit for concentrating a microorganism using the composition; a composition for extracting a nucleic acid, including DTBP as an active ingredient and a method and a kit for extracting a nucleic acid using the composition; and a composition for concentrating a microorganism and extracting a nucleic acid, including DTBP as an active ingredient and a method and a kit for concentrating a microorganism and concurrently extracting a nucleic acid from the concentrated microorganism using the composition.

Technical Solution

To solve the above problem, the present invention provides a composition for concentrating a microorganism comprising dimethyl 3,3'-dithiobispropionimidate (DTBP) as an active ingredient.

In addition, the present invention provides a kit for concentrating a microorganism comprising the composition.

Furthermore, the present invention provides a method of concentrating a microorganism, the method comprising contacting a sample including a microorganism and DTBP each other.

In addition, the present invention provides a composition for extracting a nucleic acid comprising DTBP as an active ingredient.

Furthermore, the present invention provides a kit for extracting a nucleic acid comprising the composition.

In addition, the present invention provides a method of extracting a nucleic acid, the method comprising: modifying an object by introducing an amine group into the object (step 1); injecting a sample of a nucleic acid and DTBP onto the modified object and forming a complex of the nucleic acid and the DTBP (step 2); and extracting the nucleic acid by treating the object, on which the complex is formed, with an elution buffer solution (step 3).

Furthermore, the present invention provides a composition for concentrating a microorganism and extracting a nucleic acid comprising DTBP as an active ingredient.

In addition, the present invention provides a kit for concentrating a microorganism and extracting a nucleic acid comprising the composition.

Furthermore, the present invention provides a method of concentrating a microorganism and concurrently extracting a nucleic acid from the concentrated microorganism, the method comprising: modifying an object by introducing an amine group into the object (step 1); concentrating a microorganism by contacting a sample including the microorganism and DTBP each other on the modified object (step 2); isolating a nucleic acid from the concentrated microorganism (step 3); forming a complex of the isolated nucleic acid and the DTBP (step 4); and extracting the nucleic acid by treating the object, on which the complex is formed, with an elution buffer solution (step 5).

Advantageous Effects

The present invention relates to a method of concentrating a microorganism or extracting a nucleic acid using DTBP. The present inventors have developed technology capable of concentrating a microorganism using DTBP and developed a method of directly extracting a nucleic acid from the concentrated microorganism. Technology for concentrating a microorganism and technology for extracting a nucleic acid can be realized in one tube or chip, so that it can be expected to significantly reduce pollution from the outside, a cost, a time, and complexity.

DESCRIPTION OF DRAWINGS

FIG. 1 is a schematic view illustrating a dimethyl 3,3'-dithiobispropionimidate (DTBP)/thin film Sample according to the present invention.

FIG. 2 is an exploded view illustrating a configuration of a thin film device.

FIG. 3 is a graph showing DNA extraction efficiency according to a change in DTBP concentration.

FIG. 4 is a set of views illustrating an end-point PCR (see FIG. 4A) and a real-time PCR (see FIG. 4B) of DNA extracted from a colorectal cancer cell line (HCT116 cell line, hereinafter, referred to as "HCT116").

FIG. 5 is a set of views illustrating an end-point PCR (see FIG. 5A) and a real-time PCR (see FIG. 5B) of DNA extracted from a breast cancer cell line (MCF cell line, hereinafter, referred to as "MCF").

FIG. 6 is a view illustrating a PCR result of DNA extracted from *Brucella ovis*, wherein M is a DNA marker, Q is a DNA sample extracted using an existing Qiagen method, DTBP is a DNA sample extracted using a DTBP method according to the present invention, and N is a negative control.

FIG. 7 is a set of views illustrating a method of extracting RNA (see FIG. 7A) and a method of concurrently extracting RNA and cDNA (see FIG. 7B), wherein, in FIG. 7A, an experiment is performed on the same sample four times, L is a DNA marker, and N is a negative control, and in FIG. 7B, an experiment is performed on the same sample twice and L is a DNA marker.

FIG. 8 is a graph showing a result of analyzing that a pathogen (*Escherichia coli*) is concentrated using DTBP.

FIG. 9 is a graph showing a result of concentrating a pathogen (*Escherichia coli*) and concurrently extracting and analyzing a nucleic acid in one chip using DTBP.

FIG. 10 illustrates a result of concentrating and analyzing a pathogen (RNA virus (PIV3)) using DTBP, wherein P is a positive control, N is a negative control, L is a 50 bp DNA ladder, samples 1 to 4 are DNA samples extracted using an existing Qiagen method, samples 1-1 to 4-1 are DNA samples concentrated and extracted using a DTBP method, sample 1 is diagnosed negative through the existing method, sample 1-1 concentrated using the DTBP is confirmed positive, all of samples 2 and 3 extracted through the existing method and samples 2-1 and 3-1 concentrated using the DTBP are certainly negative, and in the case of samples 4, sample 4-1 concentrated using the DTBP is confirmed to certainly increase band intensity of a sample which has been positive in the past.

BEST MODE OF THE INVENTION

The present invention provides a composition for concentrating a microorganism, which comprises dimethyl 3,3'-dithiobispropionimidate (DTBP) as an active ingredient.

Desirably, the microorganism may include all negatively charged microorganisms such as a bacterium, a virus, and a cell.

In addition, the present invention provides a kit for concentrating a microorganism, which comprises the composition. The kit may additionally include a buffer solution or the like for adjusting a pH or the like required to effectively concentrate a microorganism.

Furthermore, the present invention provides a method of concentrating a microorganism, the method comprising modifying an object by introducing an amine group into the object (step 1); and contacting a sample including the microorganism and DTBP each other on the modified object (step 2).

In the present invention, the object may have a surface which is modified with a silane compound. Desirably, the silane compound may be a compound represented by Formula 1, but the present invention is not limited thereto.

[Formula 1]

In Formula 1, $R^1$ to $R^3$ may be identical to or different from each other and be any one selected from $C_1$-$C_4$ alkyl and $C_1$-$C_4$ alkoxy, and $R^4$ may be any one selected from amino($C_1$-$C_{10}$)alkyl, 3-(2-amino($C_1$-$C_4$)alkylamino) ($C_1$-$C_4$)alkyl, and 3-[2-(2-amino($C_1$-$C_4$)alkylamino) ($C_1$-$C_4$)alkylamino] ($C_1$-$C_4$)alkyl.

More desirably, the silane compound may be at least one selected from (3-aminopropyl)triethoxysilane (APTES), (3-aminopropyl)trimethoxysilane, (1-aminomethyl)triethoxysilane, (2-aminoethyl)triethoxysilane, (4-aminobutyl)triethoxysilane, (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, [3-(2-aminoethylamino)propyl]trimethoxysilane (AEAPTMS), and 3-[(trimethoxysilyl)propyl]diethylenetriamine (TMPTA), but the present invention is not limited thereto. More desirably, the APTES or the APDMS described in an embodiment of the present invention is most suitable as the silane compound.

Desirably, the sample including the microorganism may be a sample of a feces, urine, a tear, saliva, an external secretion of skin, an external secretion of a respiratory tract, an external secretion of an intestinal tract, an external secretion of a digestive tract, plasma, serum, blood, a spinal fluid, a lymph fluid, a body fluid, or tissue of an object suspected to have been infected with the microorganism, but the present invention is not limited thereto.

In addition, the present invention provides a composition for extracting a nucleic acid, which comprises DTBP as an active ingredient. Desirably, the nucleic acid may be deoxyribonucleic acid (DNA) or ribonucleic acid (RNA), but the present invention is not limited thereto.

Furthermore, the present invention provides a kit for extracting a nucleic acid, which comprises the composition. The kit may additionally include a lysis buffer solution, a protease, or the like for dissolving a cell inside a sample to release a nucleic acid from the cell. The kit may additionally include a buffer solution or the like for adjusting a pH or the like required to effectively extract the nucleic acid.

In addition, the present invention provides a method of extracting a nucleic acid, the method comprising modifying an object by introducing an amine group into the object (step 1); injecting a sample of a nucleic acid and DTBP onto the modified object to form a complex of the nucleic acid and the DTBP (step 2); and extracting the nucleic acid by treating the object, on which the complex is formed, with an elution buffer solution (step 3).

Desirably, the object may have a surface which is modified with a silane compound. More desirably, the silane compound may be a compound represented by Formula 1, but the present invention is not limited thereto.

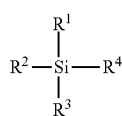

[Formula 1]

In Formula 1, $R^1$ to $R^3$ may be identical to or different from each other and be any one selected from $C_1$-$C_4$ alkyl and $C_1$-$C_4$ alkoxy, and $R^4$ may be any one selected from amino($C_1$-$C_{10}$)alkyl, 3-(2-amino($C_1$-$C_4$)alkylamino) ($C_1$-$C_4$)alkyl, and 3-[2-(2-amino($C_1$-$C_4$)alkylamino) ($C_1$-$C_4$)alkylamino] ($C_1$-$C_4$)alkyl.

More desirably, APTES or APDMS described in an embodiment of the present invention is most suitable as the silane compound.

In addition, the present invention provides a composition of concentrating a microorganism and extracting a nucleic acid, which comprises DTBP as an active ingredient.

Desirably, the microorganism may include all negatively charged microorganisms such as a bacterium, a virus, and a cell.

Desirably, the nucleic acid may be DNA or RNA, but the present invention is not limited thereto.

In addition, the present invention provides a kit for concentrating a microorganism and extracting a nucleic acid, which comprises the composition. The kit may additionally include a buffer solution or the like for adjusting a pH or the like required to effectively concentrate a microorganism and extract a nucleic acid. The kit may additionally include a lysis buffer solution, a protease, or the like for dissolving a cell inside a sample to release the nucleic acid from the cell.

In addition, the present invention provides a method of concentrating a microorganism and concurrently extracting a nucleic acid from the concentrated microorganism, the method comprising modifying an object by introducing an amine group into the object (step 1); concentrating a microorganism by contacting a sample including the microorganism and DTBP each other on the modified object (step 2); isolating a nucleic acid from the concentrated microorganism (step 3); forming a complex of the isolated nucleic acid and the DTBP (step 4); and extracting the nucleic acid by treating the object, on which the complex is formed, with an elution buffer solution (step 5).

Desirably, the object may have a surface which is modified with a silane compound. More desirably, the silane compound may be a compound represented by Formula 1, but the present invention is not limited thereto.

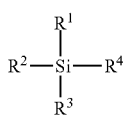

[Formula 1]

In Formula 1, $R^1$ to $R^3$ may be identical to or different from each other and be any one selected from $C_1$-$C_4$ alkyl and $C_1$-$C_4$ alkoxy, and $R^4$ may be any one selected from amino($C_1$-$C_{10}$)alkyl, 3-(2-amino($C_1$-$C_4$)alkylamino) ($C_1$-$C_4$)alkyl, and 3-[2-(2-amino($C_1$-$C_4$)alkylamino) ($C_1$-$C_4$)alkylamino] ($C_1$-$C_4$)alkyl.

More desirably, APTES or APDMS described in an embodiment of the present invention is most suitable as the silane compound.

Desirably, the sample including the microorganism may be a sample of feces, urine, a tear, saliva, an external secretion of skin, an external secretion of a respiratory tract, an external secretion of an intestinal tract, an external secretion of a digestive tract, plasma, serum, blood, a spinal fluid, a lymph fluid, a body fluid, or tissue of an object suspected to have been infected with the microorganism, but the present invention is not limited thereto In the present invention, the "object" may be any one of a thin film device, a magnetic bead, a ring resonator, and a nanoparticle, but the present invention is not limited thereto. More desirably, the object may be a thin film device which includes an upper thin film through which an inlet hole and an outlet hole described in an embodiment of the present invention are formed to pass; a lower thin film which is disposed to be spaced apart from the upper thin film; a microchannel chamber which is disposed between the upper thin film and the lower thin film, which has a microchannel patterned therein such that an inlet end and an outlet end thereof respectively correspond to communicate with the inlet hole and the outlet hole of the upper thin film, and which has an injection path formed adjacent to the inlet end so as to communicate with an inlet of the microchannel; and a sealing portion which seals sides of each of the upper thin film and the lower thin film to seal the microchannel chamber.

Hereinafter, the present invention will be described in more detail with reference to the following Examples. However, the present invention is not limited to the following Examples.

Referring to FIG. 1, a nucleic acid analysis according to the present invention is a DTBP/thin film sample analysis, which is a nucleic acid analysis using DTBP in a thin film device. The nucleic acid analysis includes three steps such as a sample eluting/incubating step, a cleaning step, and an eluting step and is performed without centrifugation. For example, the thin film device is modified with APTES as a silane compound and is converted from hydrophobicity into hydrophilicity through the modification.

A sample of a nucleic acid, an elution buffer solution, and a DTBP solution are injected onto the modified thin film device. A complex of the nucleic acid and the DTBP may be formed using a crosslinking mechanism between the nucleic acid and the DTBP through an interaction between an amino group of the nucleic acid and a bifunctional amine reactor of the DTBP, and thus, DNA may be extracted from the sample.

In this case, since the DTBP has a structure represented by Formula 2 and includes bifunctional imidoester and a disulfide bond, the DTBP forms a reversible crosslinked structure and thus is used as an amino-reactive cross-linker of a cell, a protein, and a nucleic acid. The nucleic acid may be extracted from the sample of the nucleic acid with high efficiency through rapid and strong mutual coupling between the DTBP and the nucleic acid, rather than an interaction between the DTBP and the protein.

[Formula 2]

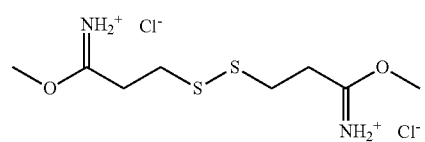

MODE OF THE INVENTION

Hereinafter, the present invention will be described in detail with reference to Examples, which are given for the understanding of the present invention and not intended to limit the scope of the present invention. The Examples of the present invention are provided for those skilled in the related art of the present invention to completely understand the present invention.

<Example 1> Manufacture and Pretreatment of Thin Film Device

1. Manufacture of Thin Film Device

A thin film device according to the present invention was manufactured using a laser cutting device (manufactured by Universal Laser Systems in Scottsdale, USA) (see FIG. 2A). First, the thin film device includes an upper thin film, a lower thin film, and a microfluidic chamber interposed between the upper thin film and the lower thin film. The microfluidic chamber includes a plurality of slot-type microwells connected to each other through a channel in the chamber in order to extract DNA from a nucleic acid source.

In order to manufacture the microfluidic chamber, a microfluidic chamber design on a 300-μm thick double-side tape (including a 100-μm thick polyester film inserted between 100-μm thick double-side tapes) was cut using the laser cutting device, thereby manufacturing the microfluidic chamber. The (upper and lower) thin films were cut to have the same size as the microfluidic chamber using the laser cutting device.

An inlet and an outlet, which are through-holes, were formed in the upper thin film. The laser-cut (upper and lower) thin films were respectively attached to upper and lower surfaces of the laser-cut microfluidic chamber using a permanent adhesive. The microfluidic chamber had a height of about 300 μm and a total volume of 300 μl (volume of 300 μl, 8.4 cm×3.7 cm).

A 3-mm thick cast acrylic sheet (MARGA CIPTA made in Indonesia) was attached to one surface of the double-side tape and was cut and perforated using the laser cutting device, thereby manufacturing a tubing adapter for injecting the nucleic acid source. The manufactured tubing adapter was attached to each of an inlet and an outlet of the microfluidic chamber. Thereafter, a precut Tygon tubing (AAC02548 manufactured by Cole-Parmer in Vernon Hills, USA) was placed in a hole of the adapter and then was sealed using epoxy.

The manufactured thin film device may treat various volumes of 100 μl, 300 μl, and 500 μl of samples of a nucleic acid.

2. Pretreatment of Thin Film Device

In order to analyze DNA using the thin film device, the inside of the thin film device was treated with oxygen plasma for 10 minutes, and the thin film device treated with the plasma was dipped in an aqueous solution including 2% APTES at a temperature of 65° C. for 10-60 minutes and then was completely cleaned with deionized water. After the cleaning, in order to cure the thin film device, the cleaned thin film device was quickly dried in a nitrogen stream to modify the thin film device with amine.

It could be seen that hydrophilicity of the thin film device was significantly changed according to temperature and an incubation time through measurement of a water contact angle of the amine-modified thin film device using a drop shape analyzer (DSA100 manufactured by KRUSS, Germany). After the thin film device was silanized with APTES at a temperature of 65° C. for 10 minutes, the surface hydrophilicity of the thin film was increased (at about 30° C. to about 40° C.).

<Example 2> DTBP/Thin Film Sample Analysis

In the present invention, a nucleic acid analysis method, in which DTBP was applied to the previously manufactured thin film device was referred to as a DTBP analysis, and the DTBP analysis was performed in the following experiment.

That is, an optimized analytical solution was primarily prepared to extract DNA using the thin film device (volume of 300 μl, 8.4 cm×3.7 cm) which was previously modified with amine. The optimized analytical solution was prepared by mixing an elution buffer solution including 10 mM tris-HCl (having a pH of 8.0), 10 nm EDTA, 1% SDS, and 10% triton X-100 with DTBP (100 mg/ml), and then, 100 μl of a nucleic analysis sample, i.e., a sample derived from a cell, a bacterium, blood, or urine was mixed with 200 μl of the analytical solution.

The mixed solution, in which the nucleic acid analysis sample and the analytical solution were mixed, was introduced through an inlet of an upper substrate of the thin film device modified with amine and was moved into the microfluidic chamber. Thus, two amine groups of the DTBP were combined with DNA, and also, the amine group in the modified thin film device was combined with the DNA to form a complex, thereby isolating DNA. In this case, in order to sufficiently extract the DNA from the nucleic acid analysis sample, the thin film device was placed in any one of an incubator and a thermoelectric cooler (TEC) including a controller (manufactured by Alpha Omega Instruments Corporation), which was maintained at a temperature of 56° C. for 20 minutes.

The DTBP-DNA complex was cleaned with a PBS buffer solution to remove foreign substances from the DTBP-DNA complex, and then, DNA was extracted using an elution buffer solution (10 mM sodium bicarbonate having a pH of 10.6). After an amount and purity of the extracted DNA were measured, an optical density ratio of the sample was determined at 260 nm (DNA) and 280 nm (protein) using an Enspire Multimode Plate Reader (manufactured by Perkin-Elmer). In order to compare the existing DNA extraction method with the DTBP analysis of the present invention, an analysis was performed using a QIAamp DNA mini kit (manufactured by Qiagen in Hilden, Germany) according to a known method.

As shown in FIG. 3, as a result of confirming a binding force for each DTBP concentration, when the DTBP concentration was 100 mg/ml, it was confirmed that DNA binding efficiency was the highest.

<Example 3> DNA Extraction from Eukaryotic Cell Using DTBP Analysis

After each of two eukaryotic cells such as HCT116 and MCF was incubated in a plastic culture plate including a high-glucose Dulbecco's modified Eagle medium (DMEM manufactured by DMEM Life Technology) supplemented with 10% fetal calf serum (hereinafter, referred to as "FCS") in a 37° C. humidified incubator maintained in a 5% $CO_2$ atmosphere, DNA was extracted from the eukaryotic cell in the same manner as in Example 1, and protease K, which is a proteolytic enzyme, was treated to extract genomic DNA. For a comparison, DNA was extracted from the eukaryotic cell using a QIAamp DNA mini kit. The HCT116 and the MCF used in the present Example were purchased from ATCC (www.atcc.org) in USA.

An end-point polymerase chain reaction (PCR) and a real-time PCR were performed to confirm an amount and purity of DNA. Forward and reverse primers of some genes (actin) were synthesized to have a normal length of about 24 base pairs. Conditions of the end-point PCR were as follows: an initial denaturation step at a temperature of 95° C. for 15 minutes; 45 cycles at a temperature of 95° C. for 45 seconds (actin), at a temperature of 59° C. for 45 seconds, and at a temperature of 72° C. for 45 seconds; and a final extension step at a temperature of 72° C. for 10 minutes. 5-10 μl of DNA was amplified in the total volume of 25 μl of a mixture including a 1×PCR buffer solution (manufactured by Qiagen), 2.5 mM magnesium chloride ($MgCl_2$), 0.25 mM deoxynucleotide triphosphate, 25 pmol each primer, and one unit of a Taq DNA polymerase.

For the real-time PCR analysis, a method provided in LightCycler 2.0 (Roche Diagnostics) was modified as follows as the next step. 5-10 μl of DNA was amplified in the total volume of 20 μl of a mixture including 4 μl of LightCycler FastStart DNA Master Mix, 25 pmol each primer, 2 μl of a 1×PCR buffer solution (manufactured by Qiagen in Hilden, Germany), 2.5 mM magnesium chloride ($MgCl_2$), 0.25 mM deoxynucleotide triphosphate, and distilled water. Initial pretreatment was performed at a temperature of 95° C. for 10 seconds, 50 cycles at a temperature of 95° C. for 10 seconds, at a temperature of 59° C. for 30 seconds (actin), and at a temperature of 72° C. for 10 seconds were performed, and then, a cooling step was performed at a temperature of 40° C. for 30 seconds. An amplification product with a SYBR green signal was treated in LightCycler 2.0 (Roche Diagnostics).

Referring to an end-point PCR (see FIG. 4A and FIG. 5A) and a real-time PCR (see FIG. 4B and FIG. 5B) of FIG. 4 and FIG. 5, in an end-point PCR result of DNA extracted using DTBP, it could be confirmed that an amount of DNA extracted from HCT116 was about 1.3 times greater than that of a case using a Qiagen product and an amount of DNA extracted from MCF was at about 2.6 times greater than that of the case using the Qiagen product. In a real-time PCR result, it could be confirmed that there was no significant difference between the DTBP and the Qiagen product.

<Example 4> DNA Extraction from Bacterial Cell Using DTBP Analysis

In order to confirm performance of a DTBP analysis with respect to a bacterial cell, PCR-based DNA amplification was performed using DNA extracted using the DTBP analysis. All primers were commercial primers of *Escherichia coli, Mycobacterium abscessus, Mycobacterium gordonae,* and *Salmonella* strains (*Salmonella Typhimurium, Salmonella* Newport, and *Salmonella* Saintpaul). Commercial primers of corresponding strains used in the present Example were purchased from IDT (www.idtdna.com) in USA.

For an optimization reaction, an elution buffer solution including 100 mM Tris-HCl (pH 8.0), 10 mM EDTA, 1% SDS, 10% triton X-100, and 20 mg/ml lysozyme were mixed with 50 mg/ml DTBP. A general PCR was performed to verify the validity of a DTBP method according to the present invention. *Escherichia coli* (*E. coli*), i.e., XL1-blue strain (purchased from Korean Collection for Type Cultures (kctc.kribb.re.kr) was inoculated into 50 μg/ml of a tetracycline and Luria-Bertani (LB) medium and was incubated in a shaking condition at a temperature of 37° C. for one day, and a sample including $10^3$ to $10^7$ colony-forming units (CFU) was used for a test. Bacteria DNA was extracted from each of *Escherichia coli, Mycobacterium abscessus, Mycobacterium gordonae,* and *Salmonella* strains (*Salmonella Typhimurium, Salmonella* Newport, *Salmonella* Saintpaul, and *Brucella ovis*), which were incubated so as to be used in a DTBP analysis and a Qiagen kit analysis. The strains used in the present Example were purchased from Korean Collection for Type Cultures (kctc.kribb.re.kr).

For a genetic analysis of bacterial genes, 2 μl of DNA extracted in the DTBP analysis and the Qiagen kit analysis was amplified at a temperature of 95° C. for 15 minutes using the total volume of 25 μl of a mixture including a 1×PCR buffer solution (manufactured by Qiagen in Hilden, Germany), 2.5 mM magnesium chloride ($MgCl_2$), 0.25 mM deoxynucleotide triphosphate, 25 pmole each primer, and one unit of a Taq DNA polymerase. Conditions of the amplification were as follows: 45 cycles at a temperature of 95° C. for 30 seconds, at a temperature of 60° C. for 30 seconds (*Mycobacterium abscessus, Mycobacterium gordonae, Salmonella* strain, and *Brucella ovis*), and at a temperature of 72° C. for 30 seconds; and a final extension step at a temperature of 72° C. for 7 minutes. PCR amplification products were visualized by gel electrophoresis, which was used to isolate PCR products on a 2% agarose gel including ethidium bromide (EtBr) (manufactured by Sigma-Aldrich). The gel was visualized using a Gel Doc System (manufactured by Bio-Rad Laboratories Inc.). A concentration and purity of DNA was measured using a UV spectrophotometer (manufactured by Perkin-Elmer)

As a result of performing a PCR analysis using DNA extracted from *Brucella ovis* using DTBP, it could be confirmed that there was no significant difference between the DTBP and a Qiagen product (FIG. 6).

<Example 5> DNA Extraction from Human Body Fluid Using DTBP Analysis

In order to verify performance of a DTBP analysis with respect to a human body fluid, 200 μl of a body fluid sample (whole blood and urine) was introduced into the thin film device to extract DNA. First, an elution buffer solution including Proteinase K and DTBP and the body fluid sample were introduced into the previously manufactured thin film device, and then, the thin film device was moved to a microchannel chamber to form a complex between DNA and DTBP in the body fluid sample, thereby extracting DNA in the same manner as in Example 2. In this case, the elution buffer solution and the body fluid sample were introduced at a flow rate of 1.5 ml/hr for 10 minutes through two different inlets using a syringe pump (manufactured by KD Scientific, MA). A cartridge was incubated at a temperature of 56° C. for 20 minutes so as to extract and purify the DNA. The flow rate in the inlet for introduction of the PBS elution buffer solution by the syringe pump was increased to 4 ml/hr for 10 minutes. Finally, the extracted DNA was eluted with 100 μl of an elution buffer solution. In addition, for a comparison, 200 μl of whole blood or urine was used to extract genomic DNA using a QIAamp DNA mini kit (manufactured by Qiagen in Hilden, Germany). A concentration and purity of all extracted DNA was determined using a UV spectrophotometer (manufactured by Perkin-Elmer).

<Example 6> RNA Extraction Using DTBP Analysis

RNA was extracted using a DTBP analysis in the same manner as in Example 2. As shown in FIG. 7A, after cDNA was externally synthesized, it was confirmed that the RNA was extracted well through 18S rRNA amplification.

As shown in FIG. 7B, the RNA extraction and the cDNA synthesis could be performed in one thin film device through a DTBP analysis, and it was confirmed later that such a method was developed well through 18S rRNA amplification.

<Example 7> Pathogen (*Escherichia coli*) Concentration and Nucleic Acid Extraction Using DTBP The previously manufactured thin film device was surface-treated with APDMS at a temperature of 65° C. for 1 hour. In order to concentrate a pathogen, 1-2 ml of a pathogen sample was injected together with 100 mg/ml DTBP and was concentrated at a flow rate of 100 µl/min at room temperature. The concentrated sample was suspended in 100 µl. In the present Example, *Escherichia coli* (*E. coli*) was used as the pathogen sample. Meanwhile, DNA was extracted with a Qiagen DNA kit, and a comparison was performed.

As a result, it was confirmed that, when concentration was performed using the DTBP, an RT-PCR Ct value was decreased to be close to an absolute value as compared with nucleic acid extraction without an concentration step using an existing Qiagen method (see FIG. 8)

On the other hand, when pathogen (*Escherichia coli*) concentration and nucleic acid extraction were performed concurrently in one chip according to the present invention, it was confirmed that the Ct value was more significantly decreased as compared with other methods and appeared to be similar to the absolute value. That is, in a method according to the present invention, it was possible to effectively concentrate the pathogen in 1-2 ml, and concurrently, it was confirmed that nucleic acid extraction efficiency was high (see FIG. 9).

<Example 8> Pathogen (RNA Virus (PIV3)) Concentration Using DTBP

In order to confirm pathogen (virus) detection efficiency of a method according to the present invention, a comparative experiment was performed on four samples suspected to have been infected with an RNA virus (PIV3) for a comparison with a Qiagen kit which is a widely used in an existing method.

That is, a case in which 1 ml of each sample was taken and extracted with the Qiagen kit to test detection of the RNA virus (PIV3) (lanes 1, 2, 3, and 4 of FIG. 10) was compared with a case in which 1 ml of each sample was concentrated and extracted to test detection of the RNA virus (lanes 1-1, 2-1, 3-1, and 4-1 of FIG. 10).

As a result, when the RNA virus (PIV3) was concentrated in 1 ml of the sample using a DTBP method, sample 1 was diagnosed negative through the existing method but sample 1-1 was confirmed positive after DTBP concentration according to the present invention. Samples 2, 3, 2-1, and 3-1 were certainly negative, and in the case of samples 4, sample 4-1 could be confirmed to certainly increase band intensity of a sample which was positive in the past (see FIG. 10).

Hereinabove, the present invention has been described by specific embodiments and drawings, but the present invention is not limited thereto and it should be understood that various changes and modifications may be made by those having ordinary skill in the art within the spirit and scope of the present invention and the appended claims and their equivalents.

The invention claimed is:

1. A method of concentrating a bacterium, a cell, or a RNA virus (PIV3), the method comprising, in order as recited:
    modifying an object by introducing an amine group into the object (step 1); and
    contacting a sample including the bacterium, the cell, or the RNA virus (PIV3) and dimethyl 3,3'-dithiobispropionimidate (DTBP) each other on the modified object (step 2).

2. The method of claim 1, wherein the object is any one of a thin film device, a magnetic bead, a ring resonator, and a nanoparticle.

3. The method of claim 1, wherein the object has a surface which is modified with a silane compound containing the amine group.

4. The method of claim 3, wherein the silane compound is a compound represented by Formula 1 below:

[Formula 1]

wherein, in Formula 1, $R^1$ to $R^3$ are identical to or different from each other and are any one selected from $C_1$-$C_4$ alkyl and $C_1$-$C_4$ alkoxy, and $R^4$ is any one selected from amino($C_1$-$C_{10}$)alkyl, 3-(2-amino($C_1$-$C_4$) alkylamino) ($C_1$-$C_4$)alkyl, and 3-[2-(2-amino($C_1$-$C_4$) alkylamino) ($C_1$-$C_4$)alkylamino] ($C_1$-$C_4$)alkyl.

5. The method of claim 4, wherein the silane compound is any one selected from the group consisting of (3-aminopropyl)triethoxysilane (APTES), (3-aminopropyl) trimethoxysilane, (1-aminomethyl)triethoxysilane, (2-aminoethyl)triethoxysilane, (4-aminobutyl)triethoxysilane, (5-aminopentyl)triethoxysilane, (6-aminohexyl)triethoxysilane, 3-aminopropyl(diethoxy)methylsilane (APDMS), N-[3-(trimethoxysilyl)propyl]ethylenediamine, [3-(2-aminoethylamino)propyl]trimethoxysilane (AEAPTMS), and 3-[(trimethoxysilyl)propyl]diethylenetriamine (TMPTA).

6. The method of claim 1, wherein the sample including the bacterium, the cell, or the RNA virus (PIV3) is any one selected from the group consisting of feces, urine, a tear, saliva, an external secretion of skin, an external secretion of a respiratory tract, an external secretion of an intestinal tract, an external secretion of a digestive tract, plasma, serum, blood, a spinal fluid, a lymph fluid, a body fluid, and tissue of an object suspected to have been infected with the bacterium, the cell, or the RNA virus (PIV3).

7. A method of concentrating a bacterium, a cell, or a RNA virus (PIV3) and concurrently extracting a nucleic acid from the concentrated bacterium, cell, or RNA virus (PIV3) comprising, in order as recited:
    modifying an object by introducing an amine group into the object (step 1);
    concentrating the bacterium, the cell, or the RNA virus (PIV3) by contacting a sample including the bacterium, the cell, or the RNA virus (PIV3) and dimethyl 3,3'-dithiobispropionimidate (DTBP) each other on the modified object (step 2);

isolating a nucleic acid from the concentrated bacterium, cell, or RNA virus (PIV3) (step 3);
forming a complex of the isolated nucleic acid and the DTBP (step 4); and
extracting the nucleic acid by treating the object, on which the complex is formed, with an elution buffer solution (step 5).

8. The method of claim 7, wherein the object has a surface which is treated with a silane compound containing the amine group.

9. The method of claim 8, wherein the silane compound is a compound represented by Formula 1 below:

[Formula 1]

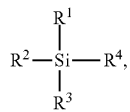

wherein, in Formula 1, $R^1$ to $R^3$ are identical to or different from each other and are any one selected from $C_1$-$C_4$ alkyl and $C_1$-$C_4$ alkoxy, and $R^4$ is any one selected from amino($C_1$-$C_{10}$)alkyl, 3-(2-amino($C_1$-$C_4$) alkylamino) ($C_1$-$C_4$)alkyl, and 3-[2-(2-amino($C_1$-$C_4$) alkylamino) ($C_1$-$C_4$)alkylamino] ($C_1$-$C_4$)alkyl.

10. The method of claim 9, wherein the silane compound is any one selected from the group consisting of (3-aminopropyl)triethoxysilane (APTES), (3-aminopropyl)trimethoxysilane, (1-aminomethyl)triethoxysilane, (2-aminoethyl)triethoxysilane, (4-aminobutyl)triethoxysilane, (5-aminopentyl)triethoxysilane, (6-aminohexyl)triethoxysilane, 3-aminopropyl(diethoxy)methyl silane (APDMS), N-[3-(trimethoxysilyl)propyl]ethylenediamine, [3-(2-aminoethylamino)propyl]trimethoxysilane (AEAPTMS), and 3-[(trimethoxysilyl)propyl]diethylenetriamine (TMPTA).

11. The method of claim 7, wherein the sample including the bacterium, the cell, or the RNA virus (PIV3) is any one selected from the group consisting of feces, urine, a tear, saliva, an external secretion of skin, an external secretion of a respiratory tract, an external secretion of an intestinal tract, an external secretion of a digestive tract, plasma, serum, blood, a spinal fluid, a lymph fluid, a body fluid, and tissue of an object suspected to have been infected with the bacterium, the cell, or the RNA virus (PIV3).

* * * * *